United States Patent
Tally et al.

(10) Patent No.: US 9,370,348 B2
(45) Date of Patent: Jun. 21, 2016

(54) DILATOR DELIVERED NERVE SHIELD

(71) Applicant: Amendia, Inc., Marietta, GA (US)

(72) Inventors: William Tally, Athens, GA (US); Kenneth Barra, Acworth, GA (US)

(73) Assignee: Amendia, Inc., Marietta, GA (US)

( * ) Notice: Subject to any disclaimer, the term of this patent is extended or adjusted under 35 U.S.C. 154(b) by 289 days.

(21) Appl. No.: 14/059,318

(22) Filed: Oct. 21, 2013

(65) Prior Publication Data

US 2014/0114133 A1  Apr. 24, 2014

Related U.S. Application Data

(60) Provisional application No. 61/717,579, filed on Oct. 23, 2012.

(51) Int. Cl.
| | |
|---|---|
| *A61B 1/32* | (2006.01) |
| *A61B 17/02* | (2006.01) |
| *A61M 29/00* | (2006.01) |
| *A61N 1/36* | (2006.01) |
| *A61B 17/88* | (2006.01) |
| *A61N 1/05* | (2006.01) |
| *A61B 17/00* | (2006.01) |
| *A61B 17/16* | (2006.01) |

(52) U.S. Cl.
CPC . *A61B 17/02* (2013.01); *A61B 1/32* (2013.01); *A61B 17/88* (2013.01); *A61M 29/00* (2013.01); *A61N 1/36* (2013.01); *A61B 17/1633* (2013.01); *A61B 2017/00261* (2013.01); *A61B 2017/0262* (2013.01); *A61N 1/0551* (2013.01)

(58) Field of Classification Search
CPC .. A61B 2017/0262; A61B 17/02; A61B 1/32; A61M 29/00
USPC .................................................. 600/204, 205
See application file for complete search history.

(56) References Cited

U.S. PATENT DOCUMENTS

| | | | |
|---|---|---|---|
| 5,759,150 A | 6/1998 | Konou et al. | |
| 6,999,819 B2* | 2/2006 | Swoyer | A61N 1/0558 607/117 |
| 7,179,225 B2* | 2/2007 | Shluzas | A61B 17/3439 600/219 |
| 7,226,451 B2* | 6/2007 | Shluzas | A61B 1/00149 600/219 |
| 7,485,092 B1 | 2/2009 | Stewart et al. | |
| 7,744,612 B2* | 6/2010 | Blain | A61B 17/7071 606/152 |
| 7,909,832 B2 | 3/2011 | Michelson | |
| 8,394,129 B2* | 3/2013 | Morgenstern Lopez | A61B 17/1757 606/279 |
| 2006/0217754 A1 | 9/2006 | Boehm, Jr. et al. | |
| 2010/0010334 A1 | 1/2010 | Bleich et al. | |
| 2010/0145267 A1 | 6/2010 | Bishop et al. | |
| 2010/0331780 A1* | 12/2010 | Bellisario | A61B 17/3415 604/164.05 |
| 2011/0208226 A1 | 8/2011 | Fatone et al. | |
| 2011/0301631 A1 | 12/2011 | Gharib et al. | |
| 2011/0313286 A1 | 12/2011 | Whayne et al. | |

* cited by examiner

*Primary Examiner* — Anu Ramana
(74) *Attorney, Agent, or Firm* — David L. King

(57) ABSTRACT

A dilator delivered nerve shield assembly is presented. The dilator delivered nerve shield assembly has an elongate dilator shaft with a distal end and a proximal end. The dilator delivered nerve shield assembly also has an elongate nerve shield that is configured for simultaneous insertion with the elongate dilator shaft.

13 Claims, 7 Drawing Sheets

DILATOR DELIVERED NERVE SHIELD

CONTINUITY

This application claims the benefit of and priority to U.S. Provisional patent application No. 61/717,573 filed on Oct. 23, 2012, which is incorporated herein in its entirety.

FIELD OF THE INVENTION

This invention relates generally to spinal surgery, and more particularly to devices and methods for accessing the disc space and maintaining the operating space while keeping the nerve root out of harm's way.

BACKGROUND OF THE INVENTION

Injured intervertebral discs are generally treated with bed rest, physical therapy, modified activities, and pain medications for substantial treatment durations. There are also a number of treatments that attempt to repair injured intervertebral discs and to avoid surgical removal of injured discs. For example, disc decompression is a procedure used to remove or shrink the nucleus, thereby decompressing and decreasing the pressure on the annulus and nerves. Less invasive procedures, such as microlumbar discectomy and automated percutaneous lumbar discectomy, remove the nucleus pulposus of a vertebral disc by aspiration through a needle laterally inserted into the annulus.

Another procedure involves implanting a disc augmentation device in order to treat, delay, or prevent disc degeneration or other disc defects. Augmentation refers to both (1) annulus augmentation, which includes repair of a herniated disc, support of a damaged annulus, and closure of an annular tear, and (2) nucleus augmentation, which includes adding or removing material to the nucleus. Many conventional treatment devices and techniques, including open surgical approaches, involve muscle dissection or percutaneous procedures to pierce a portion of the disc under fluoroscopic guidance, but without direct visualization.

Several treatments also attempt to reduce discogenic pain by injecting medicaments or by lysing adhesions in the suspected injury area. However, these devices also provide little in the form of tactile sensation for the surgeon or allow the surgeon to atraumatically manipulate surrounding tissue. In general, these conventional systems rely on external visualization for the approach to the disc and thus lack any sort of real time, on-board visualization capabilities.

Accurately diagnosing back pain is often more challenging than expected and often involves a combination of a thorough patient history and physical examination, as well as a number of diagnostic tests. A major problem is the complexity of the various components of the spine, as well as the broad range of physical symptoms experienced by individual patients. In addition, the epidural space contains various elements such as fat, connective tissue, lymphatics, arteries, veins, blood, and spinal nerve roots. These anatomical elements make it difficult to treat or diagnose conditions within the epidural area because they tend to collapse around any instrument or device inserted therein. This may reduce visibility in the epidural space, and may cause inadvertent damage to nerve roots during device insertion. Also, the insertion of a visualization device may result in blocked or reduced viewing capabilities. As such, many anatomical elements within the epidural space may limit the insertion, movement, and viewing capabilities of any access, visualization, diagnostic, or therapeutic device inserted into the epidural space.

Dilators are often used to give access to the disc space while keeping the nerve root out of the surgical area. However, the surgeon is, then, limited in operating space by the space of the interior cavity of the dilator.

SUMMARY

Presented herein is a dilator delivered nerve shield assembly for use in spinal surgery. In one aspect, the dilator delivered nerve shield assembly comprises an elongate dilator shaft with a distal end and a proximal end. The dilator delivered nerve shield assembly also comprises an elongate nerve shield that is configured for simultaneous insertion with the elongate dilator shaft.

In use, the assembly can be positioned into the disc space at the desired position and rotated to a point where the exterior surface of the elongate nerve shield is adjacent the nerve root. At this point, the elongate dilator shaft may be removed, leaving the elongate nerve shield in position, shielding the nerve root from the operative area. Then, with the nerve root shielded, the surgeon can perform the necessary surgical procedure, such as, but not limited to, insertion of an inter-body cage without fear of damaging the nerve root.

Related methods of operation are also provided. Other apparatuses, methods, systems, features, and advantages of the dilator delivered nerve shield and the method of its use will be or become apparent to one with skill in the art upon examination of the following figures and detailed description. It is intended that all such additional apparatuses, methods, systems, features, and advantages be included within this description, be within the scope of the dilator delivered nerve shield and the method of its use, and be protected by the accompanying claims.

DESCRIPTION OF THE FIGURES

The accompanying drawings, which are incorporated in and constitute a part of this specification, illustrate certain aspects of the instant invention and together with the description, serve to explain, without limitation, the principles of the invention. Like reference characters used therein indicate like parts throughout the several drawings.

DESCRIPTION OF THE INVENTION

Figure 1:
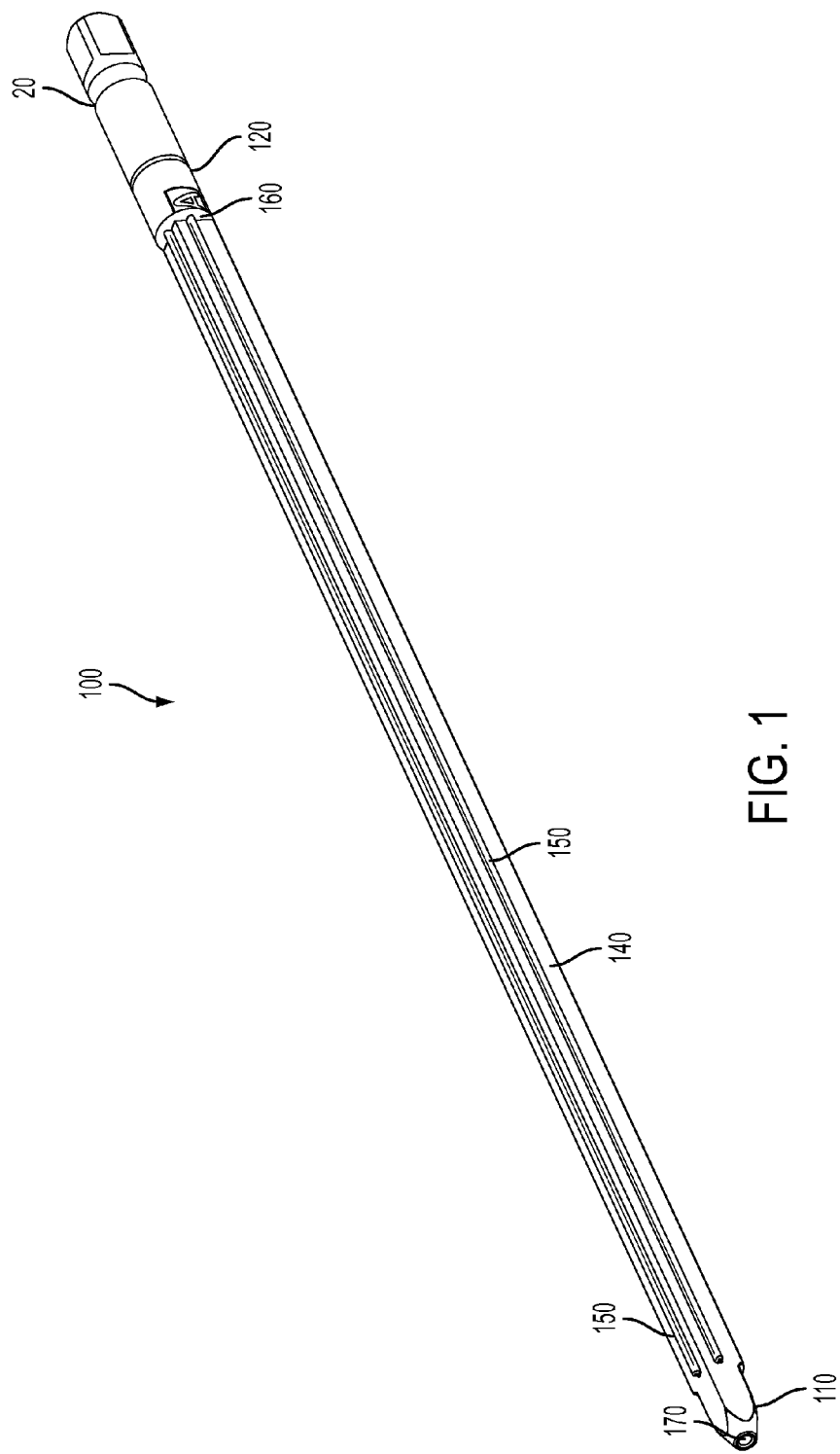
FIG. 1 is a perspective view of one aspect of an elongate dilator shaft for use with a dilator delivered nerve shield assembly.
Figure 2:
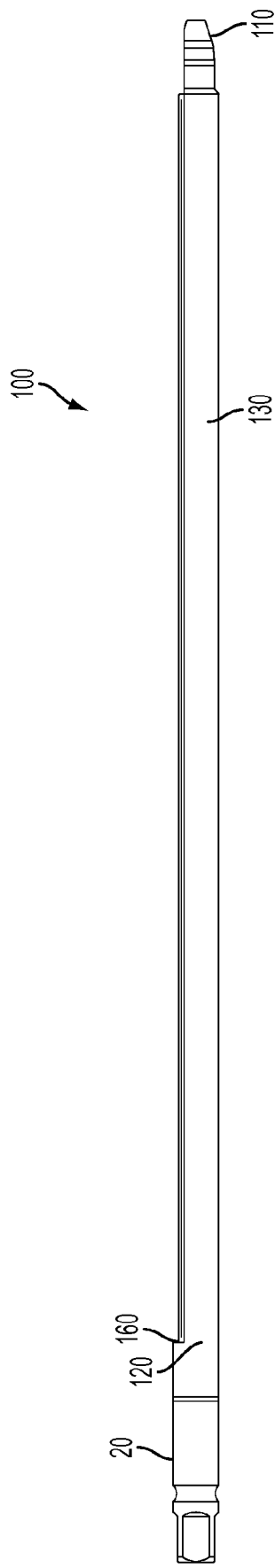
FIG. 2 is a side elevational view of the elongate dilator shaft of FIG. 1.
Figure 3:
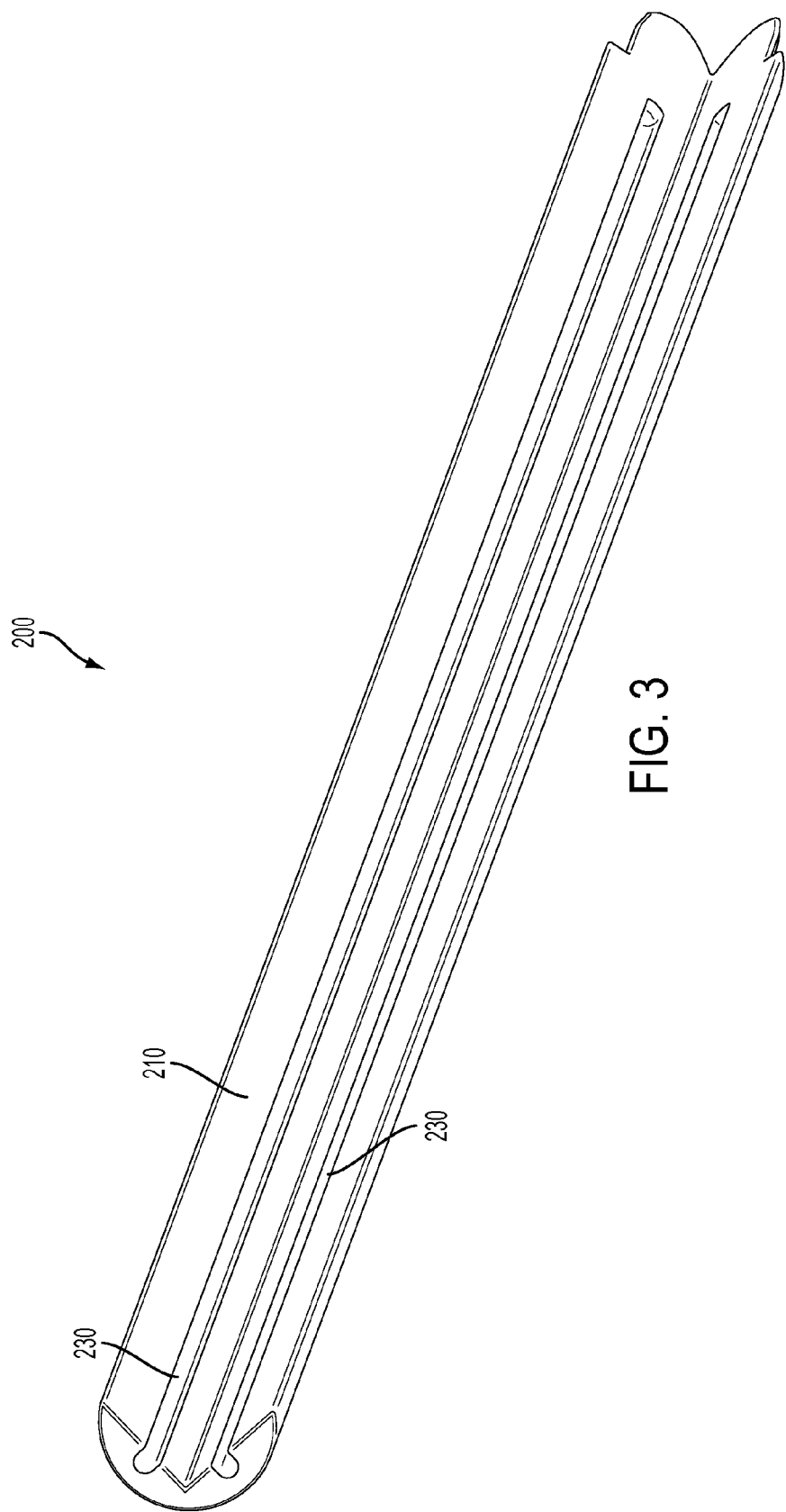
FIG. 3 is a perspective view of one aspect of an elongate nerve shield for use with a dilator delivered nerve shield assembly.
Figure 4:
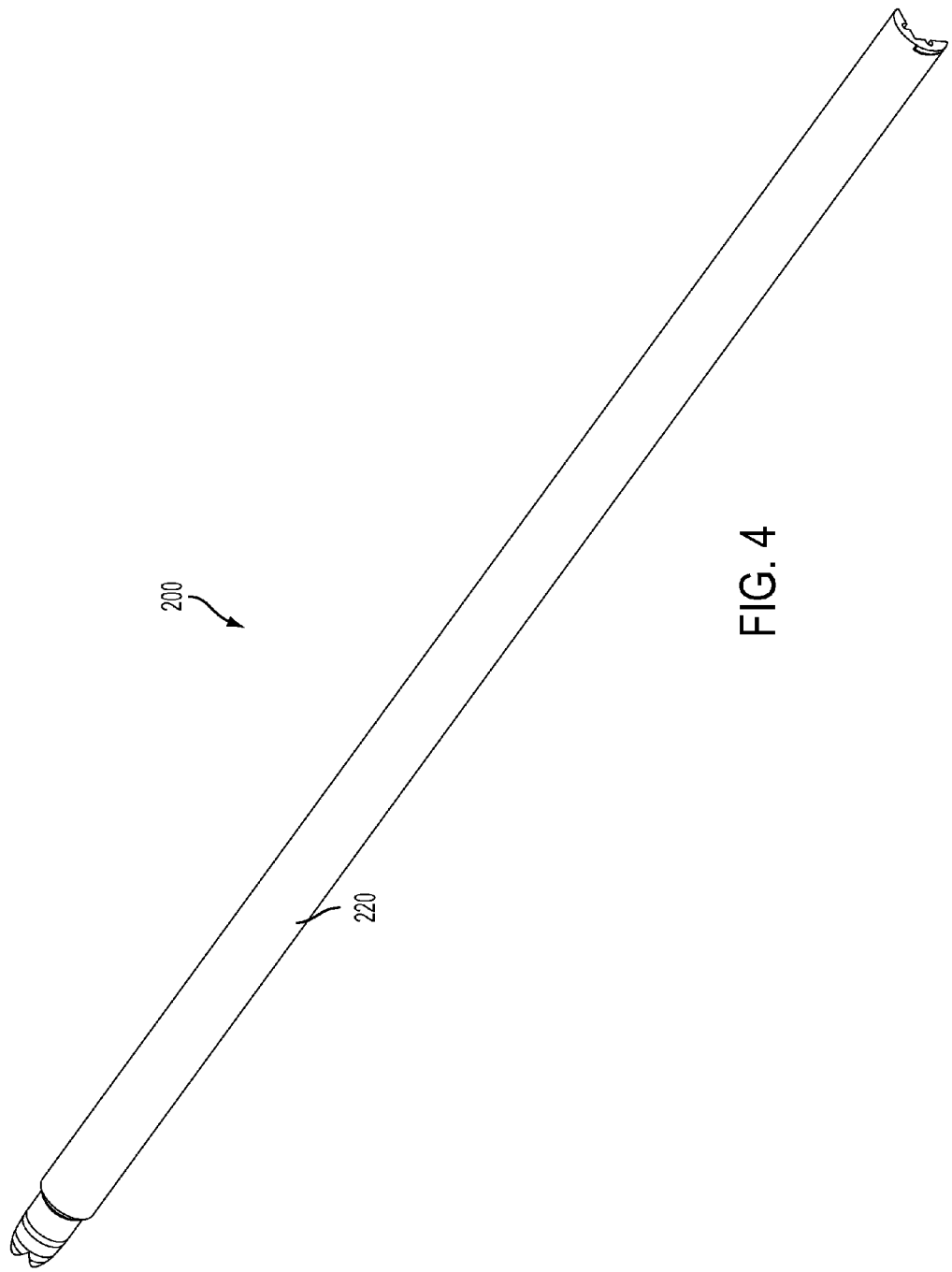
FIG. 4 is a perspective view of the elongate nerve shield of FIG. 3, showing the elongate nerve shield's exterior surface.
Figure 5:
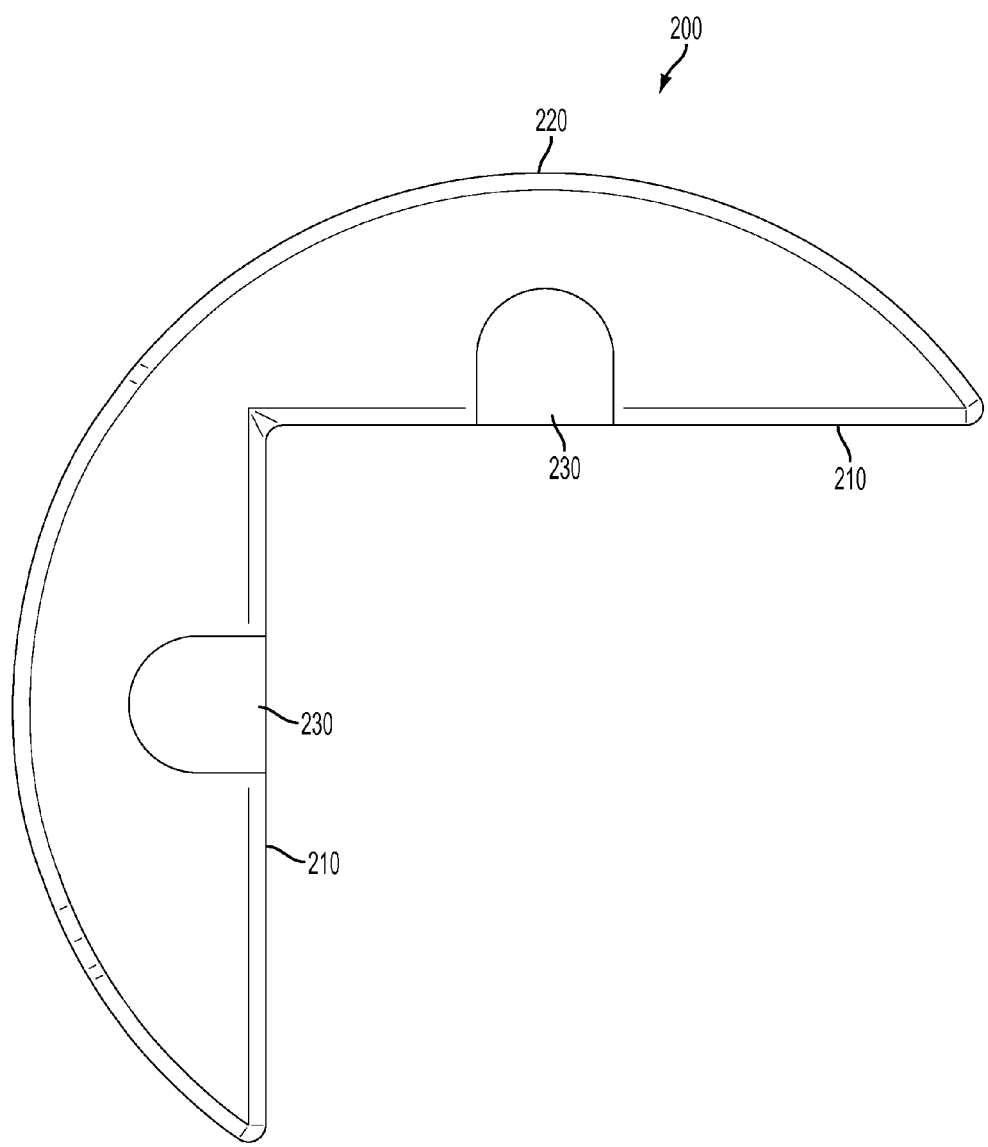
FIG. 5 is an end elevational view of the elongate nerve shield of FIG. 3.
Figure 6:
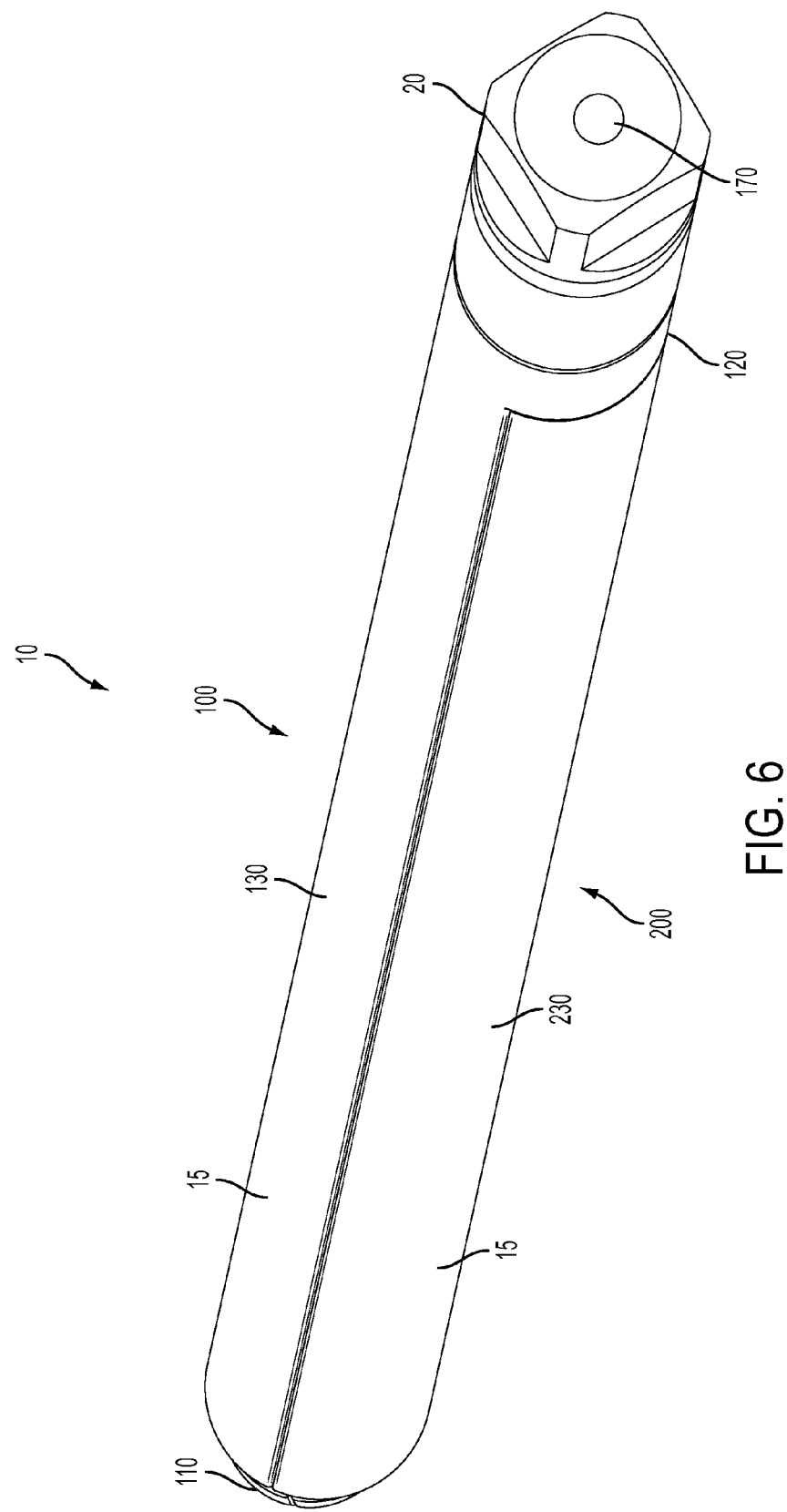
FIG. 6 is a perspective view of one aspect of a dilator delivered nerve shield assembly.
Figure 7:
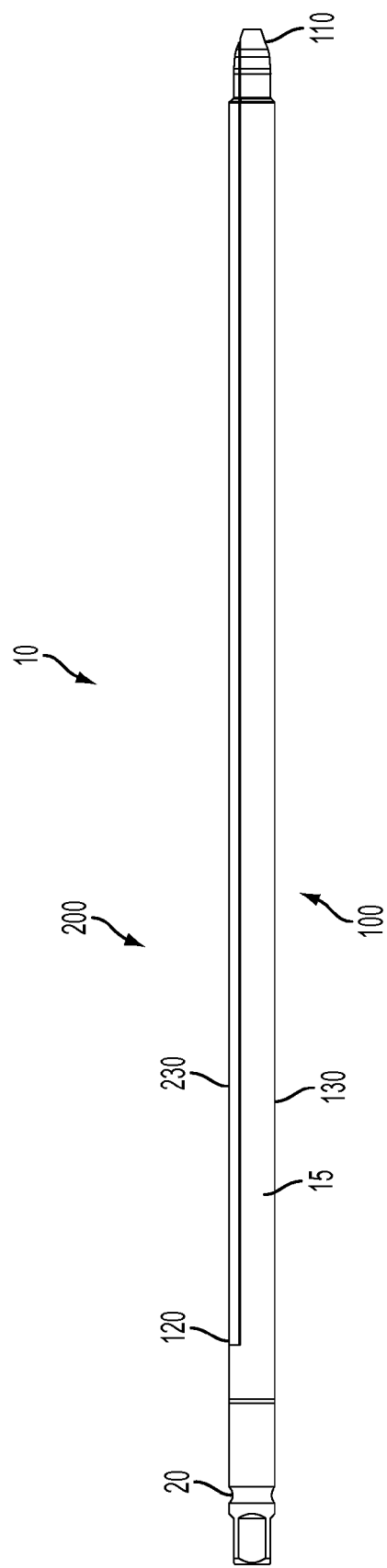
FIG. 7 is a side elevational view of the dilator delivered nerve shield assembly of FIG. 6.

The present invention can be understood more readily by reference to the following detailed description, examples, and claims, and their previous and following description. Before the present system, devices, and/or methods are disclosed and described, it is to be understood that this invention is not limited to the specific systems, devices, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known aspect. Those skilled in the relevant art will recognize that many changes can be made to the aspects described, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used herein, the singular forms "a," "an" and "the" include plural referents unless the context clearly dictates otherwise. Thus, for example, reference to a "shield" includes aspects having two or more shields unless the context clearly indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

Terms used herein, such as "exemplary" or "exemplified," are not meant to show preference, but rather to explain that the aspect discussed thereafter is merely one example of the aspect presented.

Presented herein is a dilator delivered nerve shield assembly 10 for use in spinal surgery. In one aspect, the dilator delivered nerve shield assembly 10 comprises an elongate dilator shaft 100 with a distal end 110 and a proximal end 120. In one aspect, the distal end 110 of the dilator elongate shaft is tapered to facilitate placing the elongate shaft percutaneously into the area of a desired motion segment.

The dilator delivered nerve shield assembly also comprises an elongate nerve shield 200 that is configured for simultaneous insertion with the elongate dilator shaft 100. In one aspect, the elongate dilator shaft and the elongate nerve shield 200 engage one another to form the dilator delivered nerve shield assembly that is generally cylindrical in shape as a whole. It is contemplated that other shapes can also be utilized that may be substantially tubular with various cross sectional shapes, such as, but not limited round, elliptical, square, and the like.

The elongate nerve shield is an alternative to using a circumferential access portal/refractor for delivering an intervertebral interbody past the exiting nerve root. It achieves the result of shielding the exiting nerve root on one side of the implant path, without enlarging the path.

In one aspect, the elongate dilator shaft has an exterior surface 130 and at least one engagement surface 140. In this aspect, the elongate nerve shield has an interior surface 210 and an exterior surface 220 that is complimentary to the exterior surface 130 of the elongate dilator shaft 100 elongate surface, such that, when the elongate nerve shield is engaged with the elongate dilator shaft, the exterior surfaces of the combined elongate dilator shaft 100 and elongate nerve shield 200 define the peripheral surface 15, forming the cross-sectional shape of the dilator delivered nerve shield assembly 10. For instance, if the dilator delivered nerve shield assembly has a circular cross-sectional shape, the engaged combined elongate dilator shaft and elongate nerve shield comprise the circular shape.

In another aspect, portions of the engagement surface 140 of the elongate dilator shaft are complimentarily longitudinally keyed to portions of the interior surface of the elongate nerve shield. In this manner, when engaged, the elongate nerve shield 200 can slide longitudinally with respect to the elongate dilator shaft 100, but is retained from movement radially. In one aspect, the engagement surface of the elongate dilator shaft comprises at least one longitudinal tongue 150. In this aspect, the interior surface of the elongate nerve shield defines at least one longitudinal groove 230, where the groove and tongue are configured for a mating relationship. A plurality of tongues and complimentary grooves is also contemplated. In one aspect, where at least two grooves are present, the grooves can be angled with respect to one another to prevent radial movement of the elongate nerve shield with respect to the engaging surface. In yet another aspect, the elongate tongue can comprise a keyed relationship with the elongate groove. For example, and not meant to be limiting, the two can have a dovetail shaped cross-section or a keystone shaped cross-section and the like. Other interlocking geometries that permit longitudinal movement while preventing radial movement are also contemplated. It is also contemplated that the elongate nerve shield may comprise the tongues, while the elongate shaft's engagement surface defines the grooves.

In an exemplified aspect, the assembly comprises a handle 20 connected to the proximal end 120 of the elongate dilator shaft. In one aspect, the handle and the elongate dilator shaft 100 are integral. As can be seen in the illustrations, the proximal end of the elongate dilator shaft can also comprise a stop 160 to keep an engaged elongate nerve shield 200 from moving proximally in the longitudinal direction.

In use, the assembly can be positioned into the disc space between two adjacent vertebrae at the desired position and rotated to a point where the exterior surface 220 of the elongate nerve shield is adjacent the nerve root. At this point, the elongate dilator shaft 100 may be removed, leaving the elongate nerve shield in position, shielding the nerve root from the operative field. Then, with the nerve root shielded, the surgeon can perform the necessary surgical procedure, such as, but not limited to, insertion of an inter-body cage without fear of damaging the nerve root.

In yet another aspect, the elongate dilator shaft can comprise an internal longitudinal passageway 170. In this aspect, the system can be used to perform the surgical procedure over a guide wire. The proximal end of the handle of the system may also be sized and shaped to engage a rotation tool, such as a drill, or a larger handle.

In one aspect, the elongate dilator shaft can be conductive to allow for neurostimulation of the exiting nerve root. As can be appreciated the elongate dilator shaft may comprise stainless steel or aluminum and can be deanodized to be conductive. The elongate nerve shield can, in one aspect, comprise an insulating material. For example, and not meant to be limiting, the elongate nerve shield can comprise medical grade polymer.

Although several aspects of the invention have been disclosed in the foregoing specification, it is understood by those skilled in the art that many modifications and other aspects of the invention will come to mind to which the invention pertains, having the benefit of the teaching presented in the foregoing description and associated drawings. It is thus understood that the invention is not limited to the specific aspects disclosed hereinabove, and that many modifications and other aspects are intended to be included within the scope of the appended claims. Moreover, although specific terms are employed herein, as well as in the claims that follow, they are used only in a generic and descriptive sense, and not for the purposes of limiting the described invention.

What is claimed is:

1. A dilator delivered nerve shield assembly comprising:
    an elongate dilator shaft having a distal end, a proximal end, an exterior surface, and at least one engagement surface; and
    an elongate nerve shield slidably attachable to the elongate dilator shaft having an interior surface configured to engage at least a portion of the at least one engagement surface and an exterior surface, wherein the combined exterior surface of the elongate nerve shield and the exterior surface of the elongate dilator shaft define a peripheral surface having a longitudinal extending axis and form a tubular cross-sectional shape of the dilator delivered nerve shield assembly wherein portions of the engagement surface of the elongate dilator shaft are complimentarily longitudinally keyed to portions of the interior surface of the elongate nerve shield so when the elongate nerve shield is engaged with the elongate dilator shaft the elongate nerve shield can slide longitudinally relative to the longitudinal axis with respect to the elongate dilator shaft while being retained from substantially moving radially as the dilator shaft is being removed from engagement with the elongate nerve shield wherein rotation of the assembly allows the exterior surface of the elongate nerve shield to be positioned adjacent the nerve root prior to removing the dilator shaft, the elongate nerve shield allows the implant to be inserted without enlarging an insertion path of the implant when the implant is inserted into a disc space between two adjacent vertebrae.

2. The dilator delivered nerve shield assembly of claim 1, wherein the peripheral surface forms a circular cross-sectional shape.

3. The dilator delivered nerve shield assembly of claim 1, wherein the engagement surface of the elongate dilator shaft comprises at least one longitudinal tongue extending along a longitudinal axis of the elongate dilator shaft and the interior surface of the elongate nerve shield defines at least one longitudinal groove extending along a longitudinal axis of the elongate nerve shield, and wherein the longitudinal tongue and the longitudinal groove are configured for a mating relationship.

4. The dilator delivered nerve shield assembly of claim 1, further comprises a handle connected to the proximal end of the elongate dilator shaft.

5. The dilator delivered nerve shield assembly of claim 4, wherein a proximal end of the handle is configured to engage a rotation tool.

6. The dilator delivered nerve shield assembly of claim 1, wherein the elongate dilator shaft defines an internal longitudinal passageway configured for receipt a guide wire.

7. The dilator delivered nerve shield assembly of claim 1, wherein the elongate dilator shaft is substantially conductive to allow for neurostimulation of an exiting nerve root.

8. The dilator delivered nerve shield assembly of claim 1, wherein the elongate nerve shield comprises an insulating material.

9. A method of shielding a nerve root from an operative field when performing spinal surgery, the method comprising:
    providing a dilator delivered nerve shield assembly comprising:
    an elongate dilator shaft having a distal end, a proximal end, an exterior surface, and at least one engagement surface;
    an elongate nerve shield having an interior surface configured to engage at least a portion of the at least one engagement surface and an exterior surface, wherein the exterior surface of the elongate nerve shield and the exterior surface of the elongate dilator shaft define a peripheral surface and form a cross-sectional shape of the dilator delivered nerve shield assembly;
    positioning the dilator delivered nerve shield assembly in a desired position in a disc space positioned between two adjacent vertebrae;
    rotating the dilator delivered nerve shield assembly to position the elongate nerve shield adjacent the nerve root; and
    removing the elongate dilator shaft, leaving the elongate nerve shield in position, shielding the nerve root from the operative field.

10. The method of claim 9, wherein portions of the engagement surface of the elongate dilator shaft are complimentarily longitudinally keyed to portions of the interior surface of the elongate nerve shield by a groove in the interior surface of the elongate nerve shield, the groove extending along a longitudinal axis of the elongate nerve shield and a tongue projecting from the engagement surface of the elongate dilator shaft along a longitudinal axis of the elongate dilator shaft.

11. The method of claim 10, wherein the step of removing the elongate dilator shaft comprises sliding the elongate dilator shaft longitudinally in a proximal direction with respect to the elongate dilator shaft.

12. The method of claim 9, wherein the dilator delivered nerve shield assembly further comprises a handle connected to the proximal end of the elongate dilator shaft, and wherein a proximal end of the handle is configured to engage a rotation tool.

13. The method of claim 9, further comprising performing neuro stimulation of an exiting nerve root via the elongate dilator shaft.

* * * * *